US011207711B2

(12) United States Patent
Hejazi

(10) Patent No.: US 11,207,711 B2
(45) Date of Patent: Dec. 28, 2021

(54) DETACHABLE ATOMIZATION ASSEMBLY FOR AEROSOL DELIVERY DEVICE

(71) Applicant: RAI Strategic Holdings, Inc., Winston-Salem, NC (US)

(72) Inventor: Vahid Hejazi, Concord, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 229 days.

(21) Appl. No.: 16/544,326

(22) Filed: Aug. 19, 2019

(65) Prior Publication Data

US 2021/0052014 A1 Feb. 25, 2021

(51) Int. Cl.

*A24F 13/00* (2006.01)
*B06B 1/06* (2006.01)
*A61M 11/04* (2006.01)
*A24F 7/02* (2006.01)
*A61M 11/00* (2006.01)

(52) U.S. Cl.

CPC .............. *B06B 1/0651* (2013.01); *A24F 7/02* (2013.01); *A61M 11/005* (2013.01); *A61M 11/04* (2013.01); *A61M 11/042* (2014.02); *A61M 2205/0294* (2013.01); *A61M 2205/3334* (2013.01); *A61M 2205/50* (2013.01);

(Continued)

(58) Field of Classification Search

CPC ........................................................ A24F 47/00
USPC .................................................. 131/328–329
See application file for complete search history.

(56) References Cited

U.S. PATENT DOCUMENTS

| | | | |
|---|---|---|---|
| 4,735,217 | A | 4/1988 | Gerth et al. |
| 4,947,874 | A | 8/1990 | Brooks et al. |

(Continued)

FOREIGN PATENT DOCUMENTS

| | | |
|---|---|---|
| CN | 206423575 | 8/2017 |
| EP | 3228345 | 10/2017 |

(Continued)

OTHER PUBLICATIONS

International Search Report from the corresponding International Application No. PCT/IB2020/057731, dated Oct. 29, 2020.

(Continued)

*Primary Examiner* — Phuong K Dinh

(74) *Attorney, Agent, or Firm* — Womble Bond Dickinson (US) LLP

(57) ABSTRACT

The present disclosure provides an aerosol delivery device that may comprise a housing defining an outer wall and further including a power source and a control component. The device also includes a mouthpiece portion that defines an exit aerosol path, a tank portion that includes a reservoir configured to contain a liquid composition, and an atomization assembly configured to vaporize the liquid composition to generate an aerosol. The atomization assembly includes a mesh plate and a vibrating component, wherein the mesh plate and the vibrating component are configured to be separable from each other at a detachable interface. The detachable interface may be located at various locations of the device, including between the mouthpiece portion and the tank portion, within the mouthpiece portion, within the tank portion, within a separable atomization assembly, within a cartridge, within a control unit, or between a cartridge and a control unit.

24 Claims, 5 Drawing Sheets

(52) U.S. Cl.
CPC ................. *A61M 2205/587* (2013.01); *A61M 2205/8206* (2013.01); *B06B 2201/77* (2013.01)

(56) References Cited

U.S. PATENT DOCUMENTS

| | | | |
|---|---|---|---|
| 5,154,192 | A | 10/1992 | Sprinkel et al. |
| 5,261,424 | A | 11/1993 | Sprinkel, Jr. |
| 5,372,148 | A | 12/1994 | McCafferty et al. |
| 5,934,289 | A | 8/1999 | Watkins et al. |
| 5,954,979 | A | 9/1999 | Counts et al. |
| 5,967,148 | A | 10/1999 | Harris et al. |
| 5,996,903 | A | 12/1999 | Asai et al. |
| 6,040,560 | A | 3/2000 | Fleischhauer et al. |
| 7,040,314 | B2 | 5/2006 | Nguyen et al. |
| 7,217,320 | B2 | 5/2007 | Kim et al. |
| 7,726,320 | B2 | 6/2010 | Robinson et al. |
| 8,205,622 | B2 | 6/2012 | Pan |
| 8,365,742 | B2 | 2/2013 | Hon |
| 8,402,976 | B2 | 3/2013 | Fernando et al. |
| 8,499,766 | B1 | 8/2013 | Newton |
| 8,528,569 | B1 | 9/2013 | Newton |
| 8,539,959 | B1 | 9/2013 | Scatterday |
| 8,910,640 | B2 | 12/2014 | Sears et al. |
| 8,998,483 | B2 | 4/2015 | Friend et al. |
| 9,107,453 | B2 | 8/2015 | Dube et al. |
| 9,770,055 | B2 | 9/2017 | Cameron et al. |
| 9,848,648 | B2 | 12/2017 | Memari et al. |
| 9,867,398 | B2 | 1/2018 | Guo et al. |
| 9,936,737 | B2 | 4/2018 | Cameron et al. |
| 10,004,259 | B2 | 6/2018 | Sebastian et al. |
| 2006/0196518 | A1 | 9/2006 | Hon |
| 2006/0207591 | A1 | 9/2006 | Gallem et al. |
| 2008/0084134 | A1 | 4/2008 | Morita et al. |
| 2009/0151717 | A1 | 6/2009 | Bowen et al. |
| 2009/0230117 | A1 | 9/2009 | Fernando et al. |
| 2010/0028766 | A1 | 2/2010 | Peckerar et al. |
| 2010/0163063 | A1 | 7/2010 | Fernando et al. |
| 2012/0152265 | A1 | 6/2012 | Dube et al. |
| 2013/0008457 | A1 | 1/2013 | Zheng et al. |
| 2013/0180553 | A1 | 7/2013 | Gaus et al. |
| 2013/0192623 | A1 | 8/2013 | Tucker et al. |
| 2013/0213417 | A1 | 8/2013 | Chong et al. |
| 2013/0213419 | A1 | 8/2013 | Tucker et al. |
| 2013/0255702 | A1 | 10/2013 | Griffith, Jr. et al. |
| 2013/0298905 | A1 | 11/2013 | Levin et al. |
| 2013/0319404 | A1 | 12/2013 | Feriani et al. |
| 2014/0000638 | A1 | 1/2014 | Sebastian et al. |
| 2014/0059780 | A1 | 3/2014 | Lafleche et al. |
| 2014/0060554 | A1 | 3/2014 | Collett et al. |
| 2014/0096781 | A1 | 4/2014 | Sears et al. |
| 2014/0123989 | A1 | 5/2014 | LaMothe |
| 2014/0238423 | A1 | 8/2014 | Tucker et al. |
| 2014/0261408 | A1 | 9/2014 | DePiano et al. |
| 2014/0261487 | A1 | 9/2014 | Chapman et al. |
| 2014/0261495 | A1 | 9/2014 | Novak et al. |
| 2014/0270727 | A1 | 9/2014 | Ampolini et al. |
| 2015/0020823 | A1 | 1/2015 | Lipowicz et al. |
| 2015/0020825 | A1 | 1/2015 | Galloway et al. |
| 2015/0020830 | A1 | 1/2015 | Koller |
| 2015/0034103 | A1 | 2/2015 | Hon |
| 2015/0101606 | A1 | 4/2015 | White |
| 2015/0117841 | A1 | 4/2015 | Brammer et al. |
| 2015/0216232 | A1 | 8/2015 | Bless et al. |
| 2015/0216233 | A1 | 8/2015 | Sears et al. |
| 2015/0238423 | A1 | 8/2015 | Wertz et al. |
| 2015/0245658 | A1 | 9/2015 | Worm et al. |
| 2015/0245669 | A1 | 9/2015 | Cadieux et al. |
| 2015/0257445 | A1 | 9/2015 | Henry, Jr. et al. |
| 2015/0335070 | A1 | 11/2015 | Sears et al. |
| 2016/0007561 | A9 | 1/2016 | Lipscomb |
| 2016/0158782 | A1 | 6/2016 | Henry, Jr. et al. |
| 2016/0213866 | A1 | 7/2016 | Tan |
| 2016/0262454 | A1 | 9/2016 | Sears et al. |
| 2016/0271347 | A1 | 9/2016 | Raichman |
| 2016/0366946 | A1 | 12/2016 | Murison et al. |
| 2017/0042241 | A1 | 2/2017 | Murison et al. |
| 2017/0064997 | A1 | 3/2017 | Murison et al. |
| 2017/0112191 | A1 | 4/2017 | Sur et al. |
| 2017/0112196 | A1 | 4/2017 | Sur et al. |
| 2017/0157341 | A1 | 6/2017 | Pandya et al. |
| 2017/0188626 | A1 | 7/2017 | Davis et al. |
| 2017/0238608 | A1 | 8/2017 | Matsumoto et al. |
| 2017/0303594 | A1 | 10/2017 | Cameron et al. |
| 2017/0368273 | A1 | 12/2017 | Rubin |
| 2018/0038838 | A1 | 2/2018 | Karancsi et al. |
| 2018/0090923 | A1 | 3/2018 | Li et al. |
| 2018/0153217 | A1 | 6/2018 | Liu et al. |
| 2018/0161525 | A1 | 6/2018 | Liu et al. |
| 2018/0169691 | A1 | 6/2018 | MacLoughlin et al. |
| 2018/0289076 | A1 | 10/2018 | Manca et al. |
| 2019/0014819 | A1 | 1/2019 | Sur |
| 2020/0268057 | A1 * | 8/2020 | Sahin .................... A24F 40/485 |

FOREIGN PATENT DOCUMENTS

| | | | |
|---|---|---|---|
| EP | 3272237 | | 1/2018 |
| EP | 3278678 | | 2/2018 |
| EP | 3287019 | | 2/2018 |
| EP | 3298912 | | 3/2018 |
| EP | 3305104 | | 4/2018 |
| GB | 2556759 | | 6/2018 |
| WO | WO2010003480 | | 1/2010 |
| WO | 2014/072808 | A2 | 5/2014 |
| WO | 2014/097939 | A1 | 6/2014 |
| WO | WO2014182736 | | 11/2014 |
| WO | 2015/004449 | A1 | 1/2015 |
| WO | WO2016165055 | | 10/2016 |
| WO | WO2017051181 | | 3/2017 |
| WO | WO2017063256 | | 4/2017 |
| WO | WO2017149165 | | 9/2017 |
| WO | WO2017175218 | | 10/2017 |
| WO | WO2017201710 | | 11/2017 |
| WO | WO2017201716 | | 11/2017 |
| WO | WO2017202014 | | 11/2017 |
| WO | WO2017206022 | | 12/2017 |
| WO | WO2017206480 | | 12/2017 |
| WO | WO2017215221 | | 12/2017 |
| WO | WO2018000756 | | 1/2018 |
| WO | WO2018000760 | | 1/2018 |
| WO | WO2018000761 | | 1/2018 |
| WO | WO2018000829 | | 1/2018 |
| WO | WO2018001105 | | 1/2018 |
| WO | WO2018001106 | | 1/2018 |
| WO | WO2018023890 | | 2/2018 |
| WO | WO2018040380 | | 3/2018 |
| WO | WO2018053955 | | 3/2018 |
| WO | WO2018058883 | | 4/2018 |
| WO | WO2018058884 | | 4/2018 |
| WO | WO2018095312 | | 5/2018 |

OTHER PUBLICATIONS

Ding et al., "Surface acoustic wave microfluidics", The Royal Society of Chemistry, Jul. 2013, pp. 3626-3649.
Yeo et al., "Ultrafast microfluidics using surface acoustic waves", American Institute of Physics, 2009, pp. 1-23.
Qi et al., "Miniature inhalation therapy platform using surface acoustic wave microfluidic atomization", The Royal Society of Chemistiy, May 2009, pp. 2184-2193.
Ariyakul et al., "Olfactory Display Using a Miniaturized Pump and a SAW Atomizer for Presenting Low-volatile Scents", IEEE Virtual Reality, 2011, pp. 193-194.
Olszewski et al., "A silicon-based MEMS vibrating mesh nebulizer for inhaled drug delivery", Procedia Engineering, 2016, pp. 1521-1524.
Hawkins et al., "Vibrating Mesh Nebulizer Reference Design", Microchip Technology Inc., 2016-2017, pp. 1-50.

* cited by examiner

DETACHABLE ATOMIZATION ASSEMBLY FOR AEROSOL DELIVERY DEVICE

TECHNOLOGICAL FIELD

The present disclosure relates to aerosol delivery devices, and more particularly to an aerosol delivery device that includes a reservoir and an atomization assembly, which may utilize electrical power to vaporize an aerosol precursor composition for the production of an aerosol. In various implementations, the aerosol precursor composition, which may incorporate materials and/or components that may be made or derived from tobacco or otherwise incorporate tobacco or other plants, may include natural or synthetic components including flavorants, and/or may include one or more medicinal components, is vaporized by the atomization assembly to produce an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices, and heat generating sources set forth in the background art described in U.S. Pat. No. 7,726,320 to Robinson et al., U.S. Pat. App. Pub. No. 2013/0255702 to Griffith Jr. et al., and U.S. Pat. App. Pub. No. 2014/0096781 to Sears et al., which are incorporated herein by reference in their entireties. See also, for example, the various types of smoking articles, aerosol delivery devices, and electrically powered sources referenced by brand name and commercial source in U.S. Pat. App. Pub. No. 2015/0216232 to Bless et al., which is incorporated herein by reference in its entirety.

However, it would be desirable to provide an aerosol delivery device with enhanced functionality. In this regard, it is desirable to provide an aerosol delivery with advantageous features.

BRIEF SUMMARY

The present disclosure relates to aerosol delivery devices, methods of forming such devices, and elements of such devices. In one implementation, the present disclosure provides an aerosol delivery device that may comprise a housing defining an outer wall, and may further include a power source and a control component, a mouthpiece portion that defines an exit aerosol path, a tank portion that includes a reservoir configured to contain a liquid composition, and an atomization assembly configured to vaporize the liquid composition to generate an aerosol. The atomization assembly may comprise a mesh plate and a vibrating component, and the mesh plate and the vibrating component may be configured to be separable from each other at a detachable interface.

In another implementation, at least one of the vibrating component and the mesh plate may be further configured to be removable from the device. In another implementation, the vibrating component and the mesh plate may be biased into contact with each other using one or more components of the device. In another implementation, the vibrating component and the mesh plate may be configured to be compressed between a pair of resilient members. In another implementation, the detachable interface may be located between the mouthpiece portion and the tank portion. In another implementation, one of the vibrating component or the mesh plate may be located in the mouthpiece portion and the other of the vibrating component or the mesh plate may be located in the tank portion. In another implementation, the detachable interface may be located within the mouthpiece portion. In another implementation, the detachable interface may be located within the tank portion. In another implementation, the mouthpiece portion and the tank portion may comprise a cartridge, the remaining portion of the housing may comprise a control unit, and the detachable interface may be located within the cartridge. In another implementation, the mouthpiece portion and the tank portion may comprise a cartridge, the remaining portion of the housing may comprise a control unit, and the detachable interface may be located within the control unit. In another implementation, the mouthpiece portion and the tank portion may comprise a cartridge, the remaining portion of the housing may comprise a control unit, and the detachable interface may be located between the cartridge and the control unit. In another implementation, one of the vibrating component or the mesh plate may be located in the cartridge and the other of the vibrating component or the mesh plate may be located in the control unit. In some implementations, the atomization assembly may be located between the mouthpiece portion and the tank portion. In some implementations, the mouthpiece portion, the tank portion, and the atomization assembly may be separable from each other. In some implementations, the detachable interface may be located in the atomization assembly.

In another implementation, the vibrating component may comprise a piezoelectric material. In another implementation, the vibrating component may comprise a piezoceramic ring. In another implementation, the mesh plate may be substantially flat. In another implementation, at least a portion of the mesh plate may be curved. In another implementation, the curved portion of the mesh plate may be convex with respect to the reservoir. In another implementation, the detachable interface may comprise at least one of a snap-fit engagement, a press-fit engagement, a threaded engagement, a magnetic engagement, and combinations thereof. In another implementation, the device may comprise an open system configured to permit refilling of additional liquid composition. In another implementation, the mouthpiece portion and the tank portion may comprise a cartridge, the remaining portion of the housing may comprise a control unit, and the device may comprise a closed system wherein the control unit is configured to accept one or more additional cartridges. In another implementation, the mesh plate may comprise a perforated plate.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as intended, namely to be combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE DRAWING(S)

In order to assist the understanding of aspects of the disclosure, reference will now be made to the appended drawings, which are not necessarily drawn to scale and in which like reference numerals refer to like elements. The drawings are provided by way of example to assist understanding of aspects of the disclosure, and should not be construed as limiting the disclosure.

DETAILED DESCRIPTION

Figure 1:
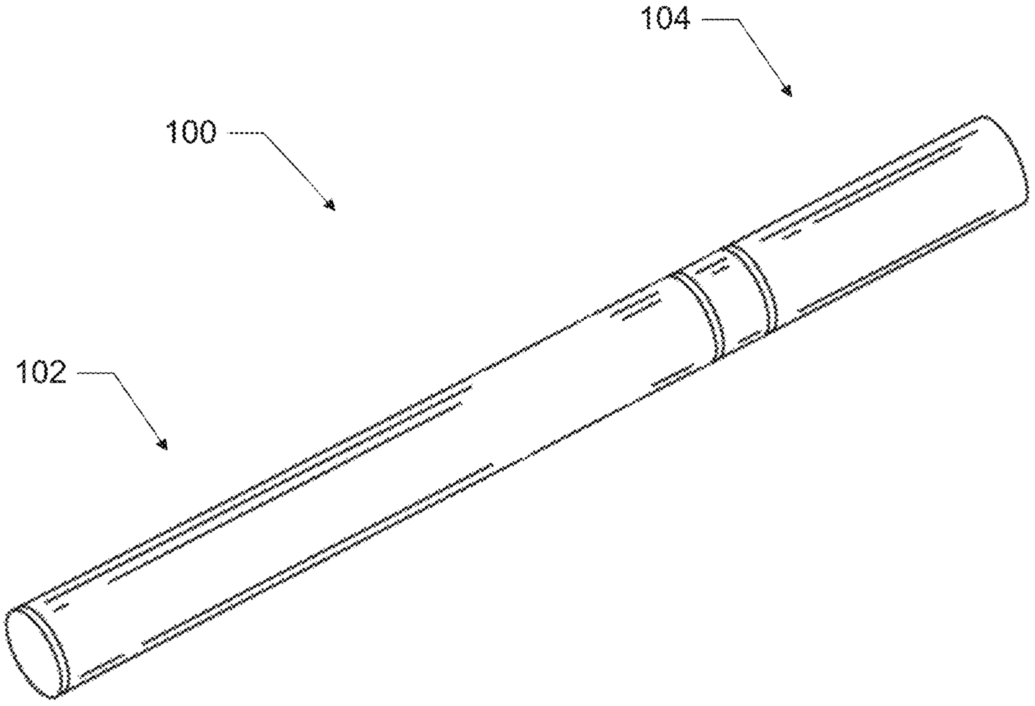
FIG. 1 is a perspective schematic view of an aerosol delivery device, according to an example implementation of the present disclosure.

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms “a”, “an”, “the”, include plural referents unless the context clearly dictates otherwise.

As described hereinafter, embodiments of the present disclosure relate to aerosol delivery devices or vaporization devices, said terms being used herein interchangeably. Aerosol delivery devices according to the present disclosure use electrical energy to vaporize a material (preferably without combusting the material to any significant degree and/or without significant chemical alteration of the material) to form an inhalable substance; and components of such devices have the form of articles that most preferably are sufficiently compact to be considered hand-held devices. That is, use of components of some aerosol delivery devices does not result in the production of smoke—i.e., from by-products of combustion or pyrolysis of tobacco, but rather, use of those systems results in the production of vapors resulting from vaporization of an aerosol precursor composition. In some embodiments, components of aerosol delivery devices may be characterized as electronic cigarettes, and those electronic cigarettes most preferably incorporate tobacco and/or components derived from tobacco, and hence deliver tobacco derived components in aerosol form. It will be appreciated, however, that devices in accordance with various embodiments can be used to deliver active ingredients other than nicotine and/or tobacco components. Other examples include delivery devices for botanical ingredients (e.g., lavender, peppermint, chamomile, basil, rosemary, thyme, eucalyptus, ginger, cannabis, ginseng, maca, and tisanes), stimulants (e.g., caffeine and guarana), amino acids (e.g., taurine, theanine, phenylalanine, tyrosine, and tryptophan) and/or pharmaceutical, nutraceutical, and medicinal ingredients (e.g., vitamins, such as B6, B12, and C and cannabinoids, such as tetrahydrocannabinol (THC) and cannabidiol (CBD)).

Aerosol generating devices of certain preferred aerosol delivery devices may provide many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe that is employed by lighting and burning tobacco (and hence inhaling tobacco smoke), without any substantial degree of combustion of any component thereof. For example, the user of an aerosol generating device of the present disclosure can hold and use the device much like a smoker employs a traditional type of smoking article, draw on one end of that device for inhalation of aerosol produced by that device, take or draw puffs at selected intervals of time, and the like.

Aerosol delivery devices of the present disclosure also may be characterized as being vapor-producing articles or medicament delivery articles. Thus, such articles or devices may be adapted so as to provide one or more substances (e.g., flavors and/or pharmaceutical active ingredients) in an inhalable form or state. For example, inhalable substances may be substantially in the form of a vapor (i.e., a substance that is in the gas phase at a temperature lower than its critical point). Alternatively, inhalable substances may be in the form of an aerosol (i.e., a suspension of fine solid particles or liquid droplets in a gas). For purposes of simplicity, the term “aerosol” as used herein is meant to include vapors, gases, and aerosols of a form or type suitable for human inhalation, whether or not visible, and whether or not of a form that might be considered to be smoke-like.

Aerosol delivery devices of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microcontroller or microprocessor), an atomization assembly, a liquid composition (e.g., commonly an aerosol precursor composition liquid capable of yielding an aerosol, such as ingredients commonly referred to as “smoke juice,” “e-liquid” and “e-juice”), and a mouthpiece or mouth region for allowing draw upon the aerosol delivery device for aerosol inhalation (e.g., a defined airflow path through the article such that aerosol generated may be withdrawn therefrom upon draw).

Alignment of the components within the aerosol delivery device may be variable. In specific embodiments, the aerosol precursor composition may be located between two opposing ends of the device (e.g., within a reservoir of a cartridge, which in certain circumstances is replaceable and disposable or refillable). Other configurations, however, are not excluded. Generally, the components are configured relative to one another so that energy from the atomization assembly vaporizes the aerosol precursor composition (as well as one or more flavorants, medicaments, or the like that may likewise be provided for delivery to a user) and forms an aerosol for delivery to the user. When the atomization assembly vaporizes the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof.

More specific formats, configurations and arrangements of components within the aerosol delivery devices of the present disclosure will be evident in light of the further disclosure provided hereinafter. Additionally, the selection and arrangement of various aerosol delivery device components may be appreciated upon consideration of the commercially available electronic aerosol delivery devices, such as those representative products referenced in the background art section of the present disclosure.

FIG. 1 illustrates an aerosol delivery device, according to an example implementation of the present disclosure. In particular, FIG. 1 illustrates a perspective schematic view of an aerosol delivery device 100 comprising a cartridge 104 and a control unit 102. As depicted in the figure, the cartridge 104 may be permanently or detachably aligned in a functioning relationship with the control unit 102. In some implementations, for example, the cartridge and the control unit may comprise a single part, whereas in other implementations (such as the depicted implementation), a connection therebetween may be releasable such that, for example, the control unit may be reused with one or more additional cartridges that may be disposable and/or refillable. In other implementations, the cartridge may not be linearly aligned with the control unit, such as implementations in which the cartridge and the control unit are in a side-by-side arrangement. In various implementations, a variety of different means of engagement may be used to couple a cartridge and a control unit together. For example, in some implementations the cartridge and the control unit may be coupled via one or more of a snap-fit engagement, a press-fit engagement, a threaded engagement, a magnetic engagement, etc. It should be noted that the components depicted in this and the other figures are representative of the components that may be present in a control unit and/or cartridge and are not intended to limit the scope of the control unit and/or cartridge components that are encompassed by the present disclosure. Some examples of mechanical and electrical connections between a cartridge and a control unit are described in U.S. patent application Ser. No. 16/386,940, filed on Apr. 17, 2019, and titled Connectors for Forming Electrical and Mechanical Connections Between Interchangeable Units in an Aerosol Delivery System, the disclosure of which is incorporated herein by reference in its entirety.

Figure 2:
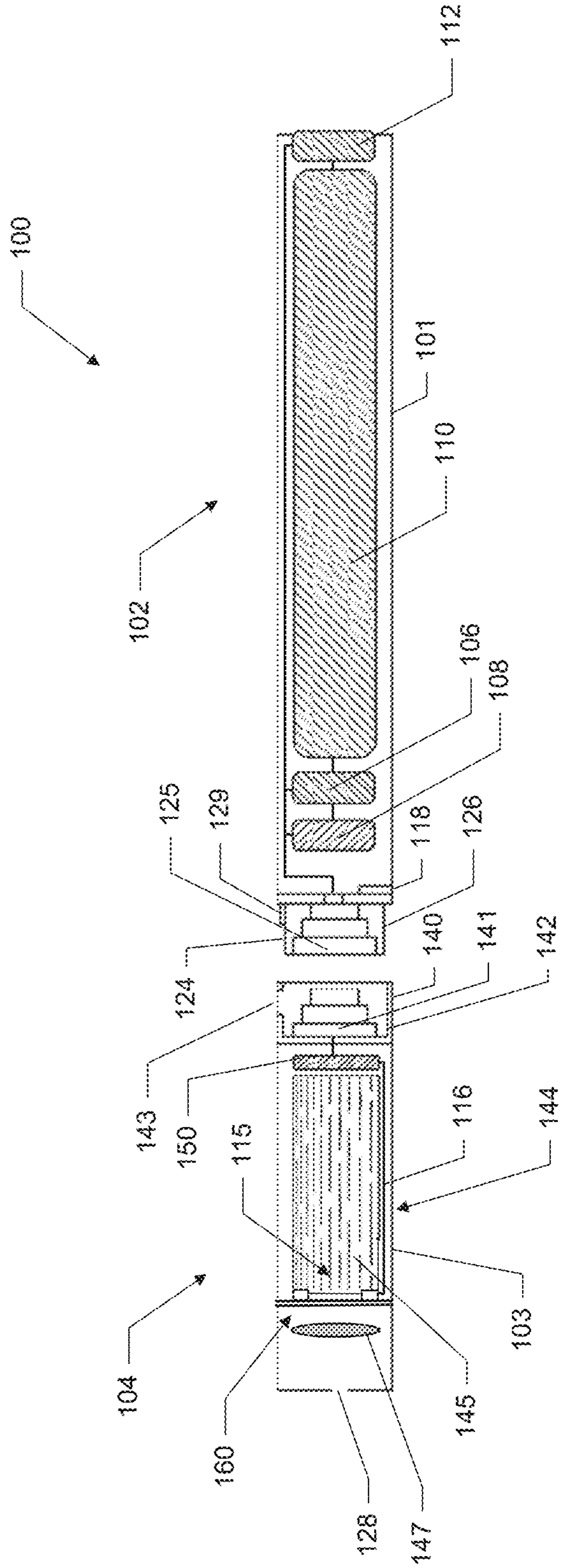
FIG. 2 illustrates a front cross-section schematic view of an aerosol delivery device, according to an example implementation of the present disclosure.

FIG. 2 illustrates a front cross-section schematic view of the aerosol delivery device 100. As depicted, the cartridge 104 and control unit 102 of FIG. 1 are shown in a de-coupled configuration. In various implementations, the aerosol delivery device 100 may have a variety of different shapes. For example, in some implementations (such as the depicted implementation) the aerosol delivery device 100 may be substantially rod-like or substantially tubular shaped or substantially cylindrically shaped. In other implementations, however, other shapes and dimensions are possible (e.g., rectangular, oval, hexagonal, prismatic, regular or irregular polygon shapes, disc-shaped, cube-shaped, multifaceted shapes, or the like). In still other implementations, the cartridge and the control unit may have different shapes. It should be noted for purposes of the present disclosure that the term “substantially” should be understood to mean approximately and/or within a certain degree of manufacturing tolerance as would be understood by one skilled in the art.

In the depicted implementation, the control unit 102 and the cartridge 104 include components adapted to facilitate mechanical engagement therebetween. Although a variety of other configurations are possible, the control unit 102 of the depicted implementation includes a coupler 124 that defines a cavity 125 therein. Likewise, the cartridge 104 includes a base 140 adapted to engage the coupler 124 of the control unit 102. A coupler and a base that may be useful according to the present disclosure are described in U.S. Pat. App. Pub. No. 2014/0261495 to Novak et al., the disclosure of which is incorporated herein by reference in its entirety.

It should be noted, however, that in other implementations various other structures, shapes, and/or components may be employed to couple the control unit and the cartridge. For example, in some implementations the control unit and cartridge may be coupled together via an interference or press fit connection such as, for example, implementations wherein the control body includes a chamber configured to receive at least a portion of the cartridge or implementations wherein the cartridge includes a chamber configured to receive at least a portion of the control unit. In other implementations, the cartridge and the control unit may be coupled together via a screw thread connection. In still other implementations, the cartridge and the control unit may be coupled together via a bayonet connection. In still other implementations, the cartridge and the control unit may be coupled via a magnetic connection. In various implementations, once coupled an electrical connection may be created between the cartridge and the control unit so as to electrically connect the cartridge (and components thereof) to the power source and/or via the control component of the control unit. Such an electrical connection may exist via one or more components of the coupling features. In such a manner, corresponding electrical contacts in the cartridge and the control unit may be substantially aligned after coupling to provide the electrical connection.

In specific implementations, one or both of the control unit 102 and the cartridge 104 may be referred to as being disposable or as being reusable. For example, in some implementations the control unit may have a power source. In some implementations, the power source may comprise a replaceable battery or a rechargeable battery and thus may be combined with any type of recharging technology, including connection to a wall charger, connection to a car charger (e.g., cigarette lighter receptacle, USB port, etc.), connection to a computer, any of which may include a universal serial bus (USB) cable or connector (e.g., USB 2.0, 3.0, 3.1, USB Type-C), connection to a USB connector (e.g., USB 2.0, 3.0, 3.1, USB Type-C as may be implemented in a wall outlet, electronic device, vehicle, etc.), connection to a photovoltaic cell (sometimes referred to as a solar cell) or solar panel of solar cells, or wireless charger, such as a charger that uses inductive wireless charging (including for example, wireless charging according to the Qi wireless charging standard from the Wireless Power Consortium (WPC)), or a wireless radio frequency (RF) based charger, and connection to an array of external cell(s) such as a power bank to charge a device via a USB connector or a wireless charger. An example of an inductive wireless charging system is described in U.S. Pat. App. Pub. No. 2017/0112196 to Sur et al., which is incorporated herein by reference in its entirety. In some implementations, the power source may comprise a photovoltaic system. In further implementations, a power source may also comprise a capacitor. Capacitors are capable of discharging more quickly than batteries and can be charged between puffs, allowing the battery to discharge into the capacitor at a lower rate than if it were used to power the heating member directly. For example, a supercapacitor—e.g., an electric double-layer capacitor (EDLC)—may be used separate from or in combination with a battery. When used alone, the supercapacitor may be recharged before each use of the article. Thus, the device may also include a charger component that can be attached to the smoking article between uses to replenish the supercapacitor. Examples of power supplies that include supercapacitors are described in U.S. Pat. App. Pub. No. 2017/0112191 to Sur et al., which is incorporated herein by reference in its entirety.

As illustrated in the figure, the control unit 102 may be formed of a control unit housing 101 that includes a control component 106 (e.g., a printed circuit board (PCB), an integrated circuit, a memory component, a microcontroller, or the like), a flow sensor 108, a battery 110, and a light-emitting diode (LED) 112, which components may be variably aligned. Some example types of electronic components, structures, and configurations thereof, features thereof, and general methods of operation thereof, are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al. and U.S. Pat. No. 8,205,622 to Pan; U.S. Pat. App. Pub. Nos. 2009/0230117 to Fernando et al., 2014/0060554 to Collet et al., and 2014/0270727 to Ampolini et al.; and U.S. Pat. App. Pub. No. 2015/0257445 to Henry et al.; which are incorporated herein by reference in their entireties. Some examples of batteries that may be applicable to the present disclosure are described in U.S. Pat. App. Pub. No. 2010/0028766 to Peckerar et al., the disclosure of which is incorporated herein by reference in its entirety. In some implementations, further indicators (e.g., a haptic feedback component, an audio feedback component, or the like) may be included in addition to or as an alternative to the LED. Additional representative types of components that yield visual cues or indicators, such as light emitting diode (LED) components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; U.S. Pat. App. Pub. No. 2015/0020825 to Galloway et al.; and U.S. Pat. App. Pub. No. 2015/0216233 to Sears et al.; which are incorporated herein by reference in their entireties. It should be understood that in various implementations not all of the illustrated elements may be required. For example, in some implementations an LED may be absent or may be replaced with a different indicator, such as a vibrating indicator. Likewise, a flow sensor may be replaced with a manual actuator, such as, for example, one or more manually actuated push buttons.

In the depicted implementation, the cartridge 104 may be formed of a cartridge housing 103, which may define a liquid reservoir 144 configured to contain a liquid composition 145. In some implementations, the liquid reservoir may be part of the cartridge housing (such as, for example, comprising a molded feature of the cartridge housing), while in other implementations, the liquid reservoir may comprise a separate part. It should be noted that while in some implementations, an aerosol delivery device of the present disclosure may comprise separate cartridge and control unit components, wherein the reservoir may or may not be refillable, in other implementations an aerosol delivery device of the present disclosure may comprise a unitary body, wherein the reservoir may or may not be refillable. As such, in some implementations, the liquid reservoir may be disposable, and in other implementations, the liquid reservoir may be refillable. In various implementations, the liquid composition contained in the liquid reservoir 144 may comprise an aerosol precursor composition. Some examples of types of substrates, reservoirs, or other components for supporting a liquid composition are described in U.S. Pat. No. 8,528,569 to Newton; U.S. Pat. App. Pub. Nos. 2014/0261487 to Chapman et al. and 2014/0059780 to Davis et al.; and U.S. Pat. App. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety.

In some implementations, the reservoir may be made of a polymeric material that, in further implementations, may be at least partially transparent or translucent. In some implementations, such materials, may include, but need not be limited to, polycarbonate, acrylic, polyethylene terephthalate (PET), amorphous copolyester (PETG), polyvinyl chloride (PVC), liquid silicone rubber (LSR), cyclic olefin copolymers, polyethylene (PE), ionomer resin, polypropylene (PP), fluorinated ethylene propylene (FEP), styrene methyl methacrylate (SMMA), styrene acrylonitrile resin (SAN), polystyrene, acrylonitrile butadiene styrene (ABS), and combinations thereof. Other materials may include, for example, biodegradable polymers such as, but not limited to, polylactcic acid (PLA), polyhydroxyalkanoates (PHA's), and polybutylene succinate (PBS). In some implementations, the reservoir may be made of other material that may be at least partially transparent or translucent. Such materials may include, for example, glass or ceramic materials.

In some implementations, the aerosol precursor composition may incorporate tobacco or components derived from tobacco. In one regard, the tobacco may be provided as parts or pieces of tobacco, such as finely ground, milled or powdered tobacco lamina. Tobacco beads, pellets, or other solid forms may be included, such as described in U.S. Pat. App. Pub. No. 2015/0335070 to Sears et al., the disclosure of which is incorporated herein by reference in its entirety. In another regard, the tobacco may be provided in the form of an extract, such as a spray dried extract that incorporates many of the water soluble components of tobacco. Alternatively, tobacco extracts may have the form of relatively high nicotine content extracts, which extracts also incorporate minor amounts of other extracted components derived from tobacco. In another regard, components derived from tobacco may be provided in a relatively pure form, such as certain flavoring agents that are derived from tobacco. In one regard, a component that is derived from tobacco, and that may be employed in a highly purified or essentially pure form, is nicotine (e.g., pharmaceutical grade nicotine, USP/EP nicotine, etc.). In other implementations, non-tobacco materials alone may form the aerosol precursor composition. In some implementations, the aerosol precursor composition may include tobacco-extracted nicotine with tobacco or non-tobacco flavors and/or non-tobacco-extracted nicotine with tobacco or non-tobacco flavors.

In the depicted implementation, the liquid composition, sometimes referred to as an aerosol precursor composition or a vapor precursor composition or "e-liquid", may comprise a variety of components, which may include, by way of example, water, a polyhydric alcohol (e.g., glycerin, propylene glycol, or a mixture thereof), nicotine, tobacco, tobacco extract, and/or flavorants. Some examples of types of aerosol precursor components and formulations are also set forth and characterized in U.S. Pat. No. 7,217,320 to Robinson et al. and U.S. Pat. App. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference in their entireties. Other aerosol precursors that may be employed include the aerosol precursors that have been incorporated in VUSE® products by R. J. Reynolds Vapor Company, the BLUM products by Fontem Ventures B.V., the MISTIC MENTHOL product by Mistic Ecigs, MARK TEN products by Nu Mark LLC, the JUUL product by Juul Labs, Inc., and VYPE products by CN Creative Ltd. Also desirable are the so-called "smoke juices" for electronic cigarettes that have been available from Johnson Creek Enterprises LLC. Still further example aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN.

The amount of aerosol precursor that is incorporated within the aerosol delivery system is such that the aerosol generating device provides acceptable sensory and desirable performance characteristics. For example, it is highly preferred that sufficient amounts of aerosol forming material (e.g., water, glycerin, and/or propylene glycol), be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating device. In one or more embodiments, about 1 ml or more, about 2 ml or more, about 5 ml or more, or about 10 ml or more of the aerosol precursor composition may be included.

In some of the examples described above, the aerosol precursor composition comprises a glycerol-based liquid. In other implementations, however, the aerosol precursor composition may be a water-based liquid. In some implementations, the water-based liquid may be comprised of more than approximately 80% water. For example, in some implementations the percentage of water in the water-based liquid may be in the inclusive range of approximately 90% to approximately 93%. In some implementations, the water-based liquid may include up to approximately 10% propylene glycol. For example, in some implementations the percentage of propylene glycol in the water-based liquid may be in the inclusive range of approximately 4% to approximately 5%. In some implementations, the water-based liquid may include up to approximately 10% flavorant. For example, in some implementations the percentage of flavorant(s) of the water-based liquid may be in the inclusive range of approximately 3% to approximately 7%. In some implementations, the water-based liquid may include up to approximately 1% nicotine. For example, in some implementations the percentage nicotine in the water-based liquid may be in the inclusive range of approximately 0.1% to approximately 0.3%. In some implementations, the water-based liquid may include up to approximately 10% cyclodextrin. For example, in some implementations the percentage cyclodextrin in the water-based liquid may be in the inclusive range of approximately 3% to 5%. In still other implementations, the aerosol precursor composition may be a combination of a glycerol-based liquid and a water-based liquid. For example, some implementations may include up to approximately 50% water and less than approximately 20% glycerol. The remaining components may include one or more of propylene glycol, flavorants, nicotine, cyclodextrin, etc. Some examples of water-based liquid compositions that may be suitable are disclosed in GB 1817863.2, filed Nov. 1, 2018, titled Aerosolisable Formulation; GB 1817864.0, filed Nov. 1, 2018, titled Aerosolisable Formulation; GB 1817867.3, filed Nov. 1, 2018, titled Aerosolisable Formulation; GB 1817865.7, filed Nov. 1, 2018, titled Aerosolisable Formulation; GB 1817859.0, filed Nov. 1, 2018, titled Aerosolisable Formulation; GB 1817866.5, filed Nov. 1, 2018, titled Aerosolisable Formulation; GB 1817861.6, filed Nov. 1, 2018, titled Gel and Crystalline Powder; GB 1817862.4, filed Nov. 1, 2018, titled Aerosolisable Formulation; GB 1817868.1, filed Nov. 1, 2018, titled Aerosolised Formulation; and GB 1817860.8, filed Nov. 1, 2018, titled Aerosolised Formulation, each of which is incorporated by reference herein in its entirety.

In some implementations, the aerosol precursor composition may incorporate nicotine, which may be present in various concentrations. The source of nicotine may vary, and the nicotine incorporated in the aerosol precursor composition may derive from a single source or a combination of two or more sources. For example, in some implementations the aerosol precursor composition may include nicotine derived from tobacco. In other implementations, the aerosol precursor composition may include nicotine derived from other organic plant sources, such as, for example, non-tobacco plant sources including plants in the Solanaceae family. In other implementations, the aerosol precursor composition may include synthetic nicotine. In some implementations, nicotine incorporated in the aerosol precursor composition may be derived from non-tobacco plant sources, such as other members of the Solanaceae family. The aerosol precursor composition may additionally or alternatively include other active ingredients including, but not limited to, botanical ingredients (e.g., lavender, peppermint, chamomile, basil, rosemary, thyme, eucalyptus, ginger, cannabis, ginseng, maca, and tisanes), stimulants (e.g., caffeine and guarana), amino acids (e.g., taurine, theanine, phenylalanine, tyrosine, and tryptophan) and/or pharmaceutical, nutraceutical, and medicinal ingredients (e.g., vitamins, such as B6, B12, and C and cannabinoids, such as tetrahydrocannabinol (THC) and cannabidiol (CBD)).

As noted above, in various implementations, the liquid composition may include a flavorant. In some implementations, the flavorant may be pre-mixed with the liquid. In other implementations, the flavorant may be delivered separately downstream from the atomizer as a main or secondary flavor. Still other implementations may combine a pre-mixed flavorant with a downstream flavorant. As used herein, reference to a “flavorant” refers to compounds or components that can be aerosolized and delivered to a user and which impart a sensory experience in terms of taste and/or aroma. Example flavorants include, but are not limited to, vanillin, ethyl vanillin, cream, tea, coffee, fruit (e.g., apple, cherry, strawberry, peach and citrus flavors, including lime and lemon, mango, and other citrus flavors), maple, menthol, mint, peppermint, spearmint, wintergreen, nutmeg, clove, lavender, cardamom, ginger, honey, anise, sage, rosemary, hibiscus, rose hip, yerba mate, guayusa, honeybush, rooibos, amaretto, mojito, yerba santa, ginseng, chamomile, turmeric, bacopa monniera, gingko biloba, withania somnifera, cinnamon, sandalwood, jasmine, cascarilla, cocoa, licorice, and flavorings and flavor packages of the type and character traditionally used for the flavoring of cigarette, cigar, and pipe tobaccos. Other examples include flavorants derived from, or simulating, burley, oriental tobacco, flue cured tobacco, etc. Syrups, such as high fructose corn syrup, also can be employed. Example plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. The selection of such further components are variable based upon factors such as the sensory characteristics that are desired for the smoking article, and the present disclosure is intended to encompass any such further components that are readily apparent to those skilled in the art of tobacco and tobacco-related or tobacco-derived products. See, e.g., Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties. It should be noted that reference to a flavorant should not be limited to any single flavorant as described above, and may, in fact, represent a combination of one or more flavorants.

Referring back to FIG. 2, the liquid reservoir 144 of the depicted implementation may be in fluid communication (either directly or through one or more additional components) with at least a portion of an atomization assembly 115. In some implementations, the liquid reservoir 144 may comprise an independent container (e.g., formed of walls substantially impermeable to the liquid composition). In some implementations, the walls of the liquid reservoir may be flexible and/or collapsible, while in other implementations the walls of the liquid reservoir may be substantially rigid. In some implementations, the liquid reservoir may be substantially sealed to prevent passage of the liquid composition therefrom except via any specific openings or conduits provided expressly for passage of the liquid composition, such as through one or more transport elements as otherwise described herein.

An electrical connection 116 connects the atomization assembly 115 to the control component 106 and/or the battery 110. In the depicted implementation, the atomization assembly 115 is connected to the base 140 of the cartridge 104, which, when assembled to the control unit 102, provides an electrical connection to the control component 106 and/or the battery 110. In such a manner, the atomization assembly 115 of the depicted implementation may be energized by the battery 110 and/or control component 106 (e.g., so as to vibrate a component of the atomization assembly at a relatively high rate). Some examples of electronic/control components that may be applicable to the present disclosure are described in U.S. Pat. App. Pub. No. 2019/0014819 to Sur, which is incorporated herein by reference in its entirety.

In various implementations, an atomization assembly may be fluidly coupled with a portion of the liquid composition such that the atomization assembly generates an aerosol from the contacted liquid composition. In various implementations, an atomization assembly may be directly fluidly coupled with a portion of the liquid composition, or indirectly fluidly coupled with a portion of the liquid composition, such as via a liquid transport element.

In various implementations, a liquid transport element may have one layer, or multiple layers, and may be made of a single material or multiple materials. In various implementations, the liquid transport element may be any shape and may be a porous, semi-porous, or non-porous absorbent/adsorbent material. In other implementations, there may be a second liquid transport element located between the first liquid transport element and the liquid reservoir, the second liquid transport element being configured to transfer liquid from the liquid reservoir to the first liquid transport element. In such a manner, the first liquid transport element may not be in direct contact with the liquid in the liquid reservoir. In various implementations, the second liquid transport element may be made of the same material or a different material than the first liquid transport element and may have a shape that is the same or differs from that of the first liquid transport element.

For example, in some implementations the liquid transport element may be made of fibrous materials (e.g., organic cotton, cellulose acetate, regenerated cellulose fabrics, glass fibers), polymers, silk, particles, porous ceramics (e.g., alumina, silica, zirconia, SiC, SiN, AlN, etc.), porous metals, porous carbon, graphite, porous glass, sintered glass beads, sintered ceramic beads, capillary tubes, porous polymers, or the like. In some implementations, the liquid transport element may be any material that contains an open pore network (i.e., a plurality of pores that are interconnected so that fluid may flow from one pore to another in a plurality of direction through the element). The pores can be nanopores, micropores, macropores or combinations thereof. As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. In some embodiments, the liquid transport element may be a substantially solid non-porous material, such as a polymer or dense ceramic or metals, configured to channel liquid through apertures or slots while not necessarily relying upon wicking through capillary action. Such a solid body may be used in combination with a porous absorptive pad. The absorptive pad may be formed of silica-based fibers, organic cotton, rayon fibers, cellulose acetate, regenerated cellulose fabrics, highly porous ceramic or metal mesh, etc. Some representative types of substrates, reservoirs or other components for supporting the aerosol precursor are described in U.S. Pat. No. 8,528,569 to Newton; U.S. Pat. App. Pub. Nos. 2014/0261487 to Chapman et al. and 2014/0059780 to Davis et al.; and U.S. Pat. App. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, the liquid transport element may be formed partially or completely from a porous monolith, such as a porous ceramic, a porous glass, or the like. Example monolithic materials that may be suitable for use according to embodiments of the present disclosure are described, for example, in U.S. Pat. App. Pub. No. 2017/0188626 to Davis et al., and U.S. Pat. App. Pub. No. 2014/0123989 to LaMothe, the disclosures of which are incorporated herein by reference in their entireties. In some implementations, the porous monolith may form a substantially solid wick.

In various implementations, an end of the liquid transport element may be configured to be placed proximate the mesh plate and between the mesh plate and liquid composition in the reservoir so that the liquid transport element acts as a secondary reservoir that absorbs or adsorbs the liquid from the reservoir so that the mesh plate is in contact with the liquid composition, even if there is no longer liquid in the reservoir. In such a manner, the liquid transport element is configured to facilitate contact between the liquid composition and the atomization assembly.

In some implementations, the liquid composition may be driven through a component of the atomization assembly resulting in the generation of a plurality of aerosol particles. Likewise, in other implementations, vibration of a component of the atomization assembly may create ultrasonic waves within the liquid composition and/or surface acoustic waves in the liquid composition, that result in the formation of an aerosol at the surface of the liquid composition. In some implementations the liquid composition may be applied and/or transferred to a component of the atomization assembly to create the aerosol. As will be described in more detail below, in various implementations two or more components of the atomization assembly may be separable from each other (and in some implementations separable from the device) at a detachable interface of the device. For example, in the implementation depicted in FIG. 1 the detachable interface 160 is located within the cartridge 104, proximate the atomization assembly 115. In other implementations, however, the detachable interface may be positioned at other locations. For example, in some implementations the detachable interface may be located between a mouthpiece portion and a tank portion of a device. In other implementations, the detachable interface may be located within a mouthpiece portion of a device. In other implementations, the detachable interface may be located within a tank portion of a device. In other implementations, the detachable interface may be located within a cartridge of a device. In other implementations, the detachable interface may be located within a control unit of a device. In other implementations, the detachable interface may be located between a cartridge and a control unit of a device. In various implementations, the separable components of an atomization assembly of the present disclosure may be included in an aerosol delivery device that comprises an open system, which is configured to permit refilling of additional liquid composition, or a closed system, wherein one component of the device may be reusable (e.g., a control unit) with one or more additional other components of the device (e.g., one or more cartridges).

In the depicted implementation, the control unit housing 101 includes an air intake 118, which may comprise an opening in the housing proximate the coupler 124 allowing for passage of ambient air into the control unit housing 101 where it then passes through the cavity 125 of the coupler 124, and eventually into or around the atomization assembly 115, where it may be mixed with the vaporized aerosol precursor composition to comprise the aerosol that is delivered to the user. It should be noted that in other implementations the air intake 118 is not limited being on or adjacent the control unit housing 101, and, in some implementations, may be located downstream from the atomization assembly. In some implementations, an air intake may be formed through the cartridge housing 103 (e.g., such that it does not enter the control unit 102) or some other portion of the aerosol delivery device 100. In the depicted implementation, a mouthpiece portion that includes an opening 128 may be present in the cartridge housing 103 (e.g., at a mouthend of the cartridge 104) to allow for egress of the formed aerosol from the cartridge 104, such as for delivery to a user drawing on the mouthend of the cartridge 104. It should be noted that some implementations need not include a mouthpiece portion and/or the mouthpiece portion may be integral with a control unit or a cartridge. As such, in some implementations the opening may be defined in the control unit or the cartridge.

In various implementations, the cartridge 104 may also include at least one electronic component 150, which may include an integrated circuit, a memory component, a sensor, or the like, although such a component need not be included. In those implementations that include such a component, the electronic component 150 may be adapted to communicate with the control component 106 and/or with an external device by wired or wireless means. In various implementations, the electronic component 150 may be positioned anywhere within the cartridge 104 or its base 140. Although in the depicted implementation the control component 106 and the flow sensor 108 are illustrated separately, it should be noted that in some implementations the control component and the flow sensor may be combined as an electronic circuit board with the air flow sensor attached directly thereto. Some examples of air flow sensors that may be applicable to the present disclosure are described in U.S. patent application Ser. No. 16/260,901, filed on Jan. 29, 2019, to Sur, the disclosure of which is incorporated herein by reference in its entirety. In some embodiments, the air flow sensor may comprise its own circuit board or other base element to which it can be attached. In some embodiments, a flexible circuit board may be utilized. A flexible circuit board may be configured into a variety of shapes, include substantially tubular shapes. Configurations of a printed circuit board and a pressure sensor, for example, are described in U.S. Pat. App. Pub. No. 2015/0245658 to Worm et al., the disclosure of which is incorporated herein by reference in its entirety. Additional types of sensing or detection mechanisms, structures, and configuration thereof, components thereof, and general methods of operation thereof, are described in U.S. Pat. No. 5,261,424 to Sprinkel, Jr.; U.S. Pat. No. 5,372,148 to McCafferty et al.; and PCT WO 2010/003480 to Flick; which are incorporated herein by reference in their entireties.

In some implementations, when a user draws on the article 100, airflow may be detected by the sensor 108, and the atomization assembly 115 may be activated, which may vaporize the liquid composition. As noted above, in some implementations drawing upon the mouthend of the article 100 causes ambient air to enter the air intake 118 and pass through the cavity 125 in the coupler 124 and the base 140. In the cartridge 104, the drawn air combines with the formed vapor to form the aerosol. The aerosol is whisked, aspirated, or otherwise drawn away from the atomization assembly 115 and out of the mouth opening 128 in the mouthend of the article 100. As noted, in other implementations, in the absence of an airflow sensor, the atomization assembly 115 may be activated manually, such as by a push button (not shown). Additionally, in some implementations, the air intake may occur through the cartridge or between the cartridge and the control unit. It should be noted that in some implementations, there may be one or more components between the atomization assembly and the opening in the mouthend of the article. For example, in the depicted implementation a heating component 147 is located downstream from the atomization assembly 115. In various implementations, the heating component may comprise any device configured to elevate the temperature of the generated aerosol, including, for example, one or more coil heating components, ceramic heating components, etc.

In some implementations, one or more input elements may be included with the aerosol delivery device (and may replace or supplement an airflow sensor, pressure sensor, or manual push button). In various implementations, an input element may be included to allow a user to control functions of the device and/or for output of information to a user. Any component or combination of components may be utilized as an input for controlling the function of the device. For example, one or more pushbuttons may be used as described in U.S. Pat. App. Pub. No. 2015/0245658 to Worm et al., which is incorporated herein by reference in its entirety. Likewise, a touchscreen may be used as described in U.S. Pat. App. Pub. No. 2016/0262454 to Sears et al., which is incorporated herein by reference in its entirety. As a further example, components adapted for gesture recognition based on specified movements of the aerosol delivery device may be used as an input. See U.S. App. Pub. No. 2016/0158782 to Henry et al., which is incorporated herein by reference in its entirety. As still a further example, a capacitive sensor may be implemented on the aerosol delivery device to enable a user to provide input, such as by touching a surface of the device on which the capacitive sensor is implemented.

In some embodiments, an input element may comprise a computer or computing device, such as a smartphone or tablet. In particular, the aerosol delivery device may be wired to the computer or other device, such as via use of a USB cord or similar protocol. The aerosol delivery device also may communicate with a computer or other device acting as an input via wireless communication. See, for example, the systems and methods for controlling a device via a read request as described in U.S. Pat. App. Pub. No. 2016/0007561 to Ampolini et al., the disclosure of which is incorporated herein by reference in its entirety. In such implementations, an APP or other computer program may be used in connection with a computer or other computing device to input control instructions to the aerosol delivery device, such control instructions including, for example, the ability to form an aerosol of specific composition by choosing the nicotine content and/or content of further flavors to be included.

Yet other features, controls or components that may be incorporated into aerosol delivery systems of the present disclosure are described in U.S. Pat. No. 5,967,148 to Harris et al.; U.S. Pat. No. 5,934,289 to Watkins et al.; U.S. Pat. No. 5,954,979 to Counts et al.; U.S. Pat. No. 6,040,560 to Fleischhauer et al.; U.S. Pat. No. 8,365,742 to Hon; U.S. Pat. No. 8,402,976 to Fernando et al.; U.S. Pat. App. Pub. Nos. 2010/0163063 to Fernando et al.; 2013/0192623 to Tucker et al.; 2013/0298905 to Leven et al.; 2013/0180553 to Kim et al., 2014/0000638 to Sebastian et al., 2014/0261495 to Novak et al., and 2014/0261408 to DePiano et al.; which are incorporated herein by reference in their entireties.

In various implementations, the atomization assembly may comprise a variety of different components or devices configured to generate an aerosol from the liquid composition. For example, in some implementations the atomization assembly may comprise a jet nebulizer assembly, which may be configured to utilize compressed air to generate an aerosol. In other implementations, the atomization assembly may comprise an ultrasonic assembly, which may be configured to utilize the formation of ultrasonic waves within the liquid composition to generate an aerosol. In other implementations, the atomization assembly may comprise a vibrating mesh assembly, which may comprise a piezoelectric material (e.g., a piezoelectric ceramic material) affixed to and substantially surrounding a mesh plate, (e.g., a perforated plate such as a micro-perforated mesh plate) that is vibrated within the liquid composition or proximate the surface of the liquid composition to generate an aerosol. In some implementations, the liquid composition may be delivered to the mesh plate (such as, for example, via a one or more liquid transport elements, and/or another delivery device such as a micropump). In other implementations, the atomization assembly may comprise a surface acoustic wave (SAW) or Raleigh wave assembly, which may utilize surface wave characteristics to generate an aerosol at the surface of the liquid composition. It should be noted that for purpose of this application, an ultrasonic assembly may be any assembly configured to create ultrasonic waves within the liquid composition. In some implementations, for example, a vibrating mesh assembly may also operate as an ultrasonic assembly.

Figure 3:
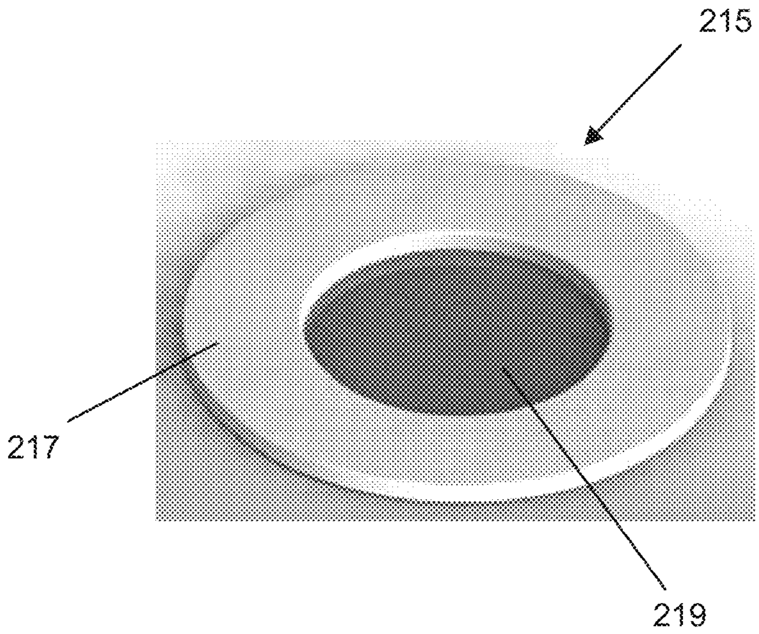
FIG. 3 illustrates a perspective view of a portion of an atomization assembly, according to an example implementation of the present disclosure.

An example of an atomization assembly of one implementation is shown in FIG. 3. In particular, FIG. 3 illustrates an atomization assembly 215 that comprises a vibrating component 217 and a mesh plate 219. In other implementations, additional components may be included. For example, in some implementations a supporting component may be included that is located on the side of the mesh plate opposite the vibrating component (e.g., such that the mesh plate is sandwiched between the supporting component and the vibrating component). Although other configurations are possible, in some implementations, the supporting component may comprise a supporting ring. In various implementations, the supporting component may be made of any suitable material, including, but not limited to, polymeric, metal, and/or ceramic materials. In such a manner, in some implementations the supporting component may increase the longevity of the mesh plate. In some implementations, the supporting component may be replaceable, while in other implementations the supporting component may be affixed to the mesh plate and/or the vibrating component. Although other configurations are possible, in some implementations, the supporting component may comprise a supporting ring. In various implementations, the supporting component may be made of any suitable material, including, but not limited to, polymeric, metal, and/or ceramic materials. In such a manner, in some implementations the supporting component may increase the longevity of the mesh plate. In some implementations, the supporting component may be replaceable, while in other implementations the supporting component may be affixed to the mesh plate and/or the vibrating component. In some implementations, an auxiliary component may be used that is located between mesh plate and the vibrating component. Although other configurations are possible, in some implementations, the auxiliary component may comprise an auxiliary ring. In various implementations, the auxiliary component may be made of any suitable material, including, but not limited to, polymeric, metal, and/or ceramic materials. In such a manner, the auxiliary component may facilitate the interfacial contact of the components. In some implementations, the auxiliary component may be replaceable, while in other implementations the auxiliary component may be affixed to the mesh plate and/or the vibrating component.

While in other implementations, the vibrating component and the mesh plate may be permanently affixed to each other such as, for example, by affixing the components together via an adhesive, such as, for example, an epoxy or other glue, or by ultrasonic welding, mechanical fasteners, etc., in the implementations depicted in the present disclosure, the vibrating component and the mesh plate are not permanently affixed to each other. Rather, they are separable and held or forced into contact with each other. In various implementations, the mesh plate may have a variety of different configurations. For example, in some implementations the mesh plate may have a substantially flat profile. In other implementations, the mesh plate may have a substantially domed shape, which may be concave or convex with respect to the reservoir and/or the liquid composition. In other implementations, the mesh plate may include a substantially flat portion and a domed portion. In various implementations, the mesh plate may be made of a variety of different materials. In some implementations, the mesh plate may be made of a metal material, such as, but not limited to, stainless steel, palladium-nickel, or titanium. In other implementations, the mesh plate may be made of a polymeric material, such as, for example, a polyimide polymer. In still other implementations, the mesh plate may be made of a combination of materials.

Figure 4A:
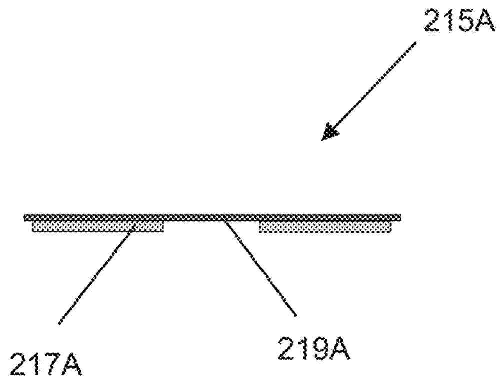
FIG. 4A illustrates a side schematic view of a portion of an atomization assembly, according to an example implementation of the present disclosure.
Figure 4B:
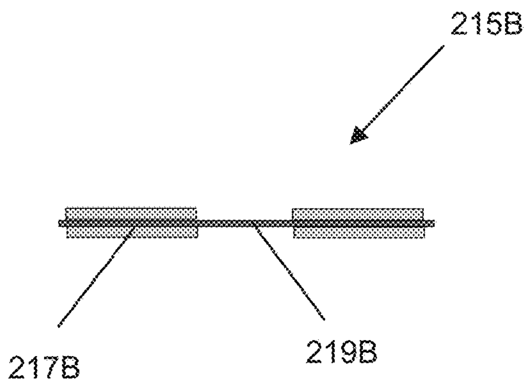
FIG. 4B illustrates a side schematic view of a portion of an atomization assembly, according to an example implementation of the present disclosure.
Figure 4C:
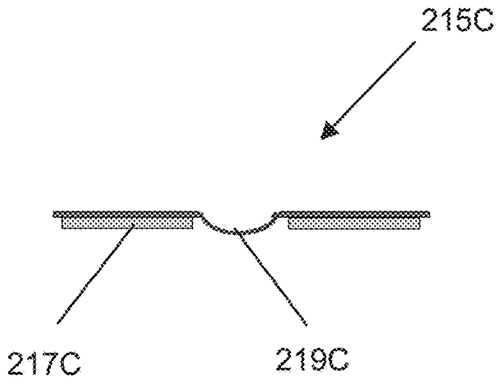
FIG. 4C illustrates a side schematic view of a portion of an atomization assembly, according to an example implementation of the present disclosure.
Figure 4D:
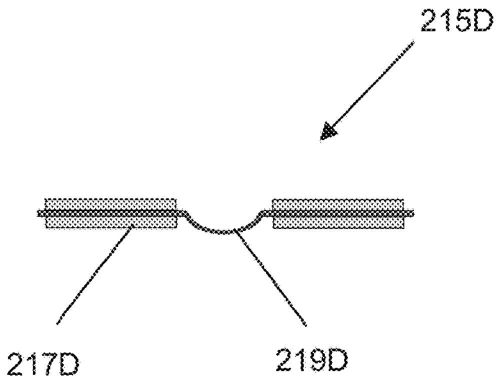
FIG. 4D illustrates a side schematic view of a portion of an atomization assembly, according to an example implementation of the present disclosure.
Figure 4E:
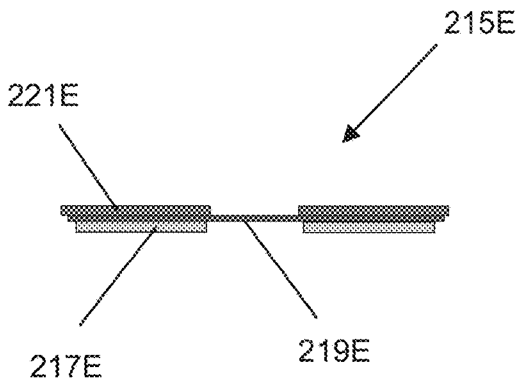
FIG. 4E illustrates a side schematic view of a portion of an atomization assembly, according to an example implementation of the present disclosure.
Figure 4F:
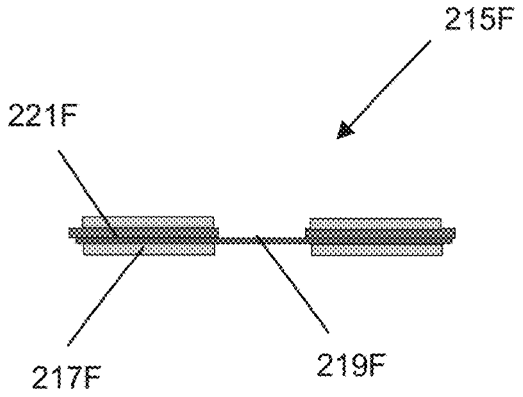
FIG. 4F illustrates a side schematic view of a portion of an atomization assembly, according to an example implementation of the present disclosure.

In various implementations, the structure of the atomization assembly may vary. For example, FIGS. 4A-4F illustrate example implementations of various atomization assemblies. In particular, FIG. 4A illustrates an atomization assembly comprising a piezoelectric ring 217A affixed to and substantially surrounding a mesh plate 219A. FIG. 4B illustrates an atomization assembly comprising a mesh plate 219A sandwiched between two portions of piezoelectric ring 217A. FIG. 4C illustrates an atomization assembly comprising a piezoelectric ring 217C affixed to and substantially surrounding a mesh plate 219C, wherein at least a portion of the mesh plate 219C is curved. FIG. 4D illustrates an atomization assembly comprising a mesh plate 219D sandwiched between two portions of a piezoelectric ring 217D, wherein at least a portion of the mesh plate 219D is curved. FIG. 4E illustrates an atomization assembly comprising a piezoelectric ring 217E affixed to and substantially surrounding one side of a mesh plate 219E, wherein the other side of the mesh plate 219E includes a metal ring 221E substantially surrounding and affixed thereto. FIG. 4F illustrates an atomization assembly comprising a mesh plate 219F one side of which includes a metal ring 221F substantially surrounding and affixed thereto, the mesh plate 219F and metal ring 221F sandwiched between two portions of a piezoelectric ring 217F.

Referring back to FIG. 3, the mesh plate 219 of the depicted implementation includes a plurality of perforations. In some implementations, the perforations may be defined by circular openings in the surfaces of the plate. In other implementations, the perforations may be defined by non-circular openings in the surfaces of the plate, such as, for example, oval, rectangular, triangular, or regular or irregular polygon openings. In various implementations, the perforations may be created using a variety of different methods, including, but not limited to, via a laser (e.g., a femtosecond laser) or via electroplating (e.g., lithography or focused ion beams) or via use of high or low energy ion or electron beams. In various implementations, the shapes defined through the plate by the perforations may vary. For example, in some implementations the shapes defined through the plate by the perforations may be substantially cylindrical. In other implementations, the shapes defined through the plate by the perforations may be substantially conical (e.g., having a truncated conical shape defining smaller openings on one surface of the plate and larger openings on the opposite surface of the plate). In other implementations, the shapes defined through the plate by the perforations may be tetragonal or pyramidal. It is believed that in some implementations, substantially conical perforations may increase the performance of the mesh in atomizing the liquid composition. Although any orientation of the mesh plate may be used, in some implementations with perforations defining substantially conical shapes through the plate, the larger openings may be located proximate the surface of the liquid composition and the smaller openings may define an aerosol outlet area. In some implementations with perforations having a substantially conical shapes, the smaller openings may have a size in the inclusive range of approximately 1 micron up to approximately 10 microns, with an average size of approximately 2 microns to approximately 5 microns. In other implementations, the smaller openings may have a size in the inclusive range of approximately several hundred nanometers up to approximately 4 microns, with an average size of approximately 2 microns to approximately 3.1 microns. In other implementations, the smaller end may have a size in the inclusive range of approximately several hundred nanometers to approximately 2 microns, with an average size of approximately 1 micron. In some implementations, the larger openings may have a size in the inclusive range of approximately 10 microns to approximately 60 microns, with an average size of approximately 20 microns to approximately 30 microns. In other implementations, the larger openings may have a size in the inclusive range of approximately 5 microns to approximately 20 microns, with an average size of approximately 10 microns. In some implementations, the size of the perforations may be substantially uniform throughout the perforated portion of the plate; however, in other implementations, the size of the perforations may vary. In such a manner, the formed aerosol may have different size aerosol droplets. For example, in some implementations the perforations may be larger in one portion of the plate and smaller in another portion of the plate. Such portions may include, for example, the center of the plate and a periphery of the plate, or alternating rings that extend radially from the center of the plate.

In various implementations, the mesh plate may have any number of perforations. In some implementations, for example, a number of perforations in the mesh plate may be in the inclusive range of approximately 200 to approximately 6,000, with an average number of perforations of approximately 1,100 to approximately 2,500. In other implementations, a number of perforations in the mesh plate may be in the inclusive range of approximately 400 to approximately 1,000. In various implementations, the thickness of the vibrating component and the thickness of the mesh plate may vary. For example, in some implementations the thickness of the mesh plate may be in the range of a few microns to a few millimeters. In various implementations, the overall diameter of a mesh plate may vary. For example, in some implementations the overall diameter of the mesh plate may be in the inclusive range of approximately a few millimeters to approximately 30 millimeters. In some implementations, the outer diameter of the vibrating component may be larger than the overall diameter of the mesh plate. In other implementations, the outer diameter of the vibrating component may be substantially the same size as the overall diameter of the mesh plate. In still other implementations, the outer diameter of the vibrating component may be smaller than the overall diameter of the mesh plate. In various implementations, the diameter of the perforation area may be smaller than the overall diameter of the mesh plate. For example, in some implementations the diameter of the perforated area may be in the inclusive range of approximately 1 millimeter to approximately 20 millimeters, with an average of approximately 4 millimeters to approximately 12 millimeters. In some implementations, the inner diameter of the vibrating component may be larger than the diameter of the perforated area of the mesh plate. In other implementations, the inner diameter of the vibrating component may be substantially the same as, or smaller than, the diameter of the perforated area of the mesh plate. In some implementations, the thickness of the vibrating component may be in the inclusive range of a few hundred microns to tens of millimeters. For example, in some implementations the thickness of the vibrating component may be smaller than 1 millimeter.

In various implementations, the vibrating component may comprise a piezoelectric component. For example, in various implementations the vibrating component may comprise a piezoelectric ring, which, in some implementations may be made of a piezoceramic material. It should be noted that while the depicted implementation describes a piezoelectric component in the form of a piezoelectric ring, in other implementations the piezoelectric component need not be limited to a ring-shaped object. For example, in some implementations the piezoelectric component may have rectangular, oval, hexagonal, triangular, and regular or irregular polygon shapes. In general, piezoceramic materials possess piezoelectric properties (e.g., ferroelectric properties), wherein they are configured to change shape to a small extent (e.g., 1-2 microns in our application) when exposed to an electrical stimulus. This occurs due to a shift in the crystal structure of the piezoceramic materials (e.g., from orthorhombic to cubic, or hexagonal to cubic, etc.). With respect to a piezoceramic ring, such a change in shape results in an internal strain and therefore shrinkage of the disc that results in bending of the disk due to its rigid structure. Because the ring is affixed to the mesh plate, the bending of the ring is transferred to the mesh material. When the electric current is disconnected from the piezoelectric ring, the ring and mesh plate return to their original shape and position. As such, a continuous change of the shape and position will result in an oscillating motion that can be used as a vibration source. In various implementations, the frequency of the piezoelectric ring may be in the range of a few Hz to several MHz. For example, in some implementations the frequency of the piezoelectric ring in in the inclusive range of approximately 50 KHz to approximately 150 KHz, with an average, in one implementation of approximately 110 KHz, in another implementation of approximately 113 KHz, in another implementation of approximately 117 KHz, in another implementation, of approximately 130 KHz, in another implementation, of approximately 150 KHz, in another implementation, of approximately 170 KHz, and in another implementation, of approximately 250 KHz. In other implementations, the frequency of the piezoelectric ring is in the inclusive range of approximately 1 MHz to approximately 5 MHz, with an average of approximately 3 MHz to approximately 3.5 MHz.

In various implementations, a variety of different piezoelectric materials are possible, including natural or synthetic materials. Some non-limiting examples of natural piezoelectric materials include, for example, quartz, berlinite ($APO_4$), sucrose, rochelle salt, topaz, tourmaline-group minerals, lead titanate ($PbTiO_3$), and collagen. Some non-limiting examples of synthetic materials include, for example, a ($La_3Ga_5SiO_{14}$), gallium phosphate, gallium orthophosphate ($GaPO_4$), lithium niobate ($LiNbO_3$), lithium tantalate ($LiTaO_3$), AlN, ZnO, barium titanate ($BaTiO_3$), lead zirconate titanate ($Pb[Zr_xTi_{1-x}]O_3$) (a.k.a. PZT), potassium niobate ($KNbO_3$), sodium tungstate ($Na_2WO_3$), $Ba_2NaNb_5O_5$, $Pb_2KNb_5O_{15}$, zinc oxide (ZnO), sodium potassium niobate ($(K,Na)NbO_3$) (a.k.a. NKN), bismuth ferrite ($BiFeO_3$), sodium niobate $NaNbO_3$, barium titanate ($BaTiO_3$), bismuth titanate $Bi_4Ti_3O_{12}$, sodium titanate, and sodium bismuth titanate $NaBi(TiO_3)_2$. In other implementations, polymers exhibiting piezoelectric characteristics may be used, including, but not limited to, polyvinylidene fluoride (PVDF).

In various implementations, the mesh plate 219 of the atomization assembly 215 may be in contact with at least a portion of a liquid composition, and/or may be proximate at least a portion of a liquid composition, and/or may receive (such as via a delivery mechanism) at least a portion of a liquid composition. In such a manner, the resulting vibration of the plate generates an aerosol from the contacted liquid composition. In particular, in some implementations, the liquid composition is driven through the plurality of micro perforations resulting in the generation of a plurality of aerosol particles. Likewise, in other implementations, such as, for example, implementations in which the mesh plate is immersed in the liquid composition, vibration of the plate creates ultrasonic waves within the liquid composition that result in the formation of an aerosol at the surface of the liquid composition. As will be described in more detail below, in other implementations the liquid composition may be applied and/or transferred to the atomization assembly to create the aerosol.

Figure 5:
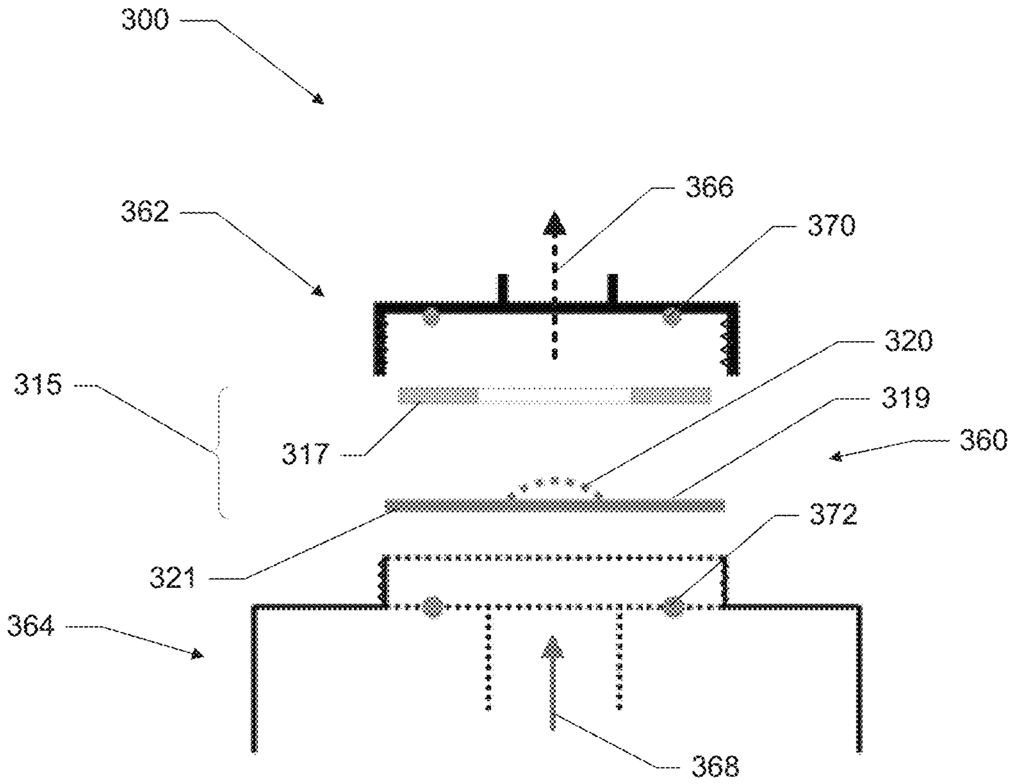
FIG. 5 illustrates a side schematic exploded view of a portion of an aerosol delivery device, according to an example implementation of the present disclosure.

Another example of a portion of an aerosol delivery device, according to an example implementation of the present disclosure, is shown in FIG. 5. In particular, FIG. 5 illustrates a side (or top, depending on point of reference) schematic exploded view of a portion of an aerosol delivery device 300. In the depicted implementation, the aerosol delivery device 300 includes a mouthpiece portion 362 and a tank portion 364. In the depicted implementation, the mouthpiece portion 362 and the tank portion 364 are configured to be coupled to and de-coupled from each other at a detachable interface 360. In various implementations, these components may be coupled and de-coupled via one or more of a snap-fit engagement, a press-fit engagement, a threaded engagement, a magnetic engagement, etc. In other implementations, these components may be coupled and de-coupled via one or more mechanical fasteners, such as, for example, one or more screws. In the depicted implementation, for example, the mouthpiece portion 362 and the tank portion 364 are coupled and de-coupled via a threaded engagement, which may include inner threads (or outer threads) on the mouthpiece portion 362 and outer threads (or inner threads) on the tank portion 364.

In the depicted implementation, an atomization assembly 315 is located between the mouthpiece portion 362 and the tank portion 364. As depicted, the mouthpiece portion 362 defines an exit aerosol path 366 through which formed aerosol is delivered to a user, and the tank portion 364 defines a channel 368, which provides fluid communication between the liquid composition and the atomization assembly 315. In the depicted implementation, the atomization assembly 315 comprises a vibrating component 317, which in some implementations may comprise a piezoelectric ring, and a mesh plate 319, which in some implementations may comprise a micro-perforated mesh plate. Although other configurations are possible, the mesh plate 319 of the depicted implementation includes a curved portion 320 (e.g., convex with respect to a reservoir) located proximate a center of the plate and a flat portion 321 located around the curved portion 320. Further reference is made to the discussion of vibrating mesh assembly components and variations described above.

In the depicted implementation, the vibrating component 317 and the mesh plate 319 are separable from each other and from the device 300 at a detachable interface 360, which is located between the mouthpiece portion 362 and the tank portion 364. Although other configurations are possible, the vibrating component 317 of the depicted implementation is located proximate the mouthpiece portion 362, above the mesh plate 319, which is located proximate the tank portion 364. Although other configurations are possible, the overall diameter of the vibrating component 317 of the depicted implementation is smaller than an overall diameter of the mesh plate 319. When assembled, the vibrating component 317 and the mesh plate 319 of the depicted implementation are biased into contact with each other. In the depicted implementation, these components are biased into contact with each other using a pair of resilient members 370, 372. As such, in the depicted implementation the vibrating component 317 and the mesh plate 319 are compressed between the pair of resilient members 370, 372. In particular, in the depicted implementation the mouthpiece portion 362 includes a first resilient member 370, which, when assembled, is configured to contact the vibrating component 317 and force the vibrating component 317 downward. Likewise, in the depicted implementation the tank portion 364 includes a second resilient member 372, which, when assembled, is configured to contact the mesh plate 319 and force the mesh plate upward. In such a manner, when the mouthpiece portion 362 is coupled to the tank portion 364, the first and second resilient members 370, 372 force the vibrating component 317 and the mesh plate 319 into contact with each other. In other implementations, an auxiliary component may be used that is located between mesh plate and the vibrating component. Although other configurations are possible, in some implementations, the auxiliary component may comprise an auxiliary ring. In various implementations, the auxiliary component may be made of any suitable material, including, but not limited to, polymeric, metal, and/or ceramic materials. In such a manner, the auxiliary component may facilitate the interfacial contact of the components. In some implementations, the auxiliary component may be replaceable, while in other implementations the auxiliary component may be affixed to the mesh plate and/or the vibrating component.

Likewise, when the mouthpiece portion 362 and the tank portion 364 are de-coupled from each other, the vibrating portion 317 and the mesh plate 319 are separable from each other and from the aerosol delivery device 300. In the depicted implementation, the first and second resilient members 370, 372 comprise O-rings made of an elastic polymer material. Example materials include, but are not limited to, polytetrafluoroethylene (PTFE), nitrile, silicone, neoprene, ethylene propylene diene monomer (EPDM) rubber, fluorocarbon, etc. In other implementations, the vibrating component and the mesh plate may be biased into contact using other force-generating means, including, for example, one or more foam or other compressible components, one or more springs, various mechanical features (e.g., angled ramp or cam features), electro-mechanical devices, and combinations thereof.

Although not shown in the figures, in some implementations the mouthpiece portion 362 may include one or more features that facilitate electrical connection with the vibrating component 317. For example, in some implementations the mouthpiece portion 362 may include electrodes that are electrically connected to the control component and/or the battery and that are configured to electrically connect to corresponding contacts of the vibrating component 317. In one implementation, for example, the mouthpiece portion 362 may include a recess having electrodes (e.g., positive and negative electrodes) defined therein. In such a manner, the vibrating component 317 may be configured to be received in the recess so that the electrodes electrically connect with corresponding contacts (e.g., positive and negative contacts) of the vibrating component 317. In some implementations, the interface between the mouthpiece portion 362 and the vibrating component 317 may be keyed or otherwise configured such that the vibrating component 317 has a specific orientation relative to the mouthpiece portion 362.

It should be noted that in other implementations, an aerosol delivery device may include a mouthpiece portion, an atomization assembly, and a tank portion, and the mouthpiece portion, the atomization assembly, and the tank portion may all separable from each other. For example, in one implementation the atomization assembly may be located between a mouthpiece portion and a tank portion such that the atomization assembly is configured to be coupled and de-coupled from both the mouthpiece portion and the tank portion. In particular, in one implementation the atomization assembly may be configured to couple and de-couple from the mouthpiece portion on one end and couple and de-couple from the tank portion on the other end.

Further, in some implementations the atomization assembly may include a mesh plate and a vibrating component, and the mesh plate and the vibrating component may be separable from each other as two subcomponents of an atomization assembly that is itself separable from a mouthpiece portion and a separate tank portion.

Although in some implementations of the present disclosure a cartridge and a control unit may be provided together as a complete aerosol delivery device generally, these components may be provided separately. For example, the present disclosure also encompasses a disposable unit for use with a reusable unit. In specific implementations, such a disposable unit (which may be a cartridge as illustrated in the appended figures) can be configured to engage a reusable unit (which may be a control unit as illustrated in the appended figures). In still other configurations, a cartridge may comprise a reusable unit and a control unit may comprise a disposable unit. In some implementations, one or more of these configurations may be beneficial for replacing one or both of the mesh plate and the vibrating component, or providing access for cleaning one or more of the components.

Although some figures described herein illustrate a cartridge and a control unit in a working relationship, it is understood that the cartridge and the control unit may exist as individual components. Accordingly, any discussion otherwise provided herein in relation to the components in combination also should be understood as applying to the control unit and the cartridge as individual and separate components.

In another aspect, the present disclosure may be directed to kits that provide a variety of components as described herein. For example, a kit may comprise a control unit with one or more cartridges. A kit may further comprise a control unit with one or more charging components. A kit may further comprise a control unit with one or more batteries. A kit may further comprise a control unit with one or more cartridges and one or more charging components and/or one or more batteries. In further implementations, a kit may comprise a plurality of cartridges. A kit may further comprise a plurality of cartridges and one or more batteries and/or one or more charging components. In the above implementations, the cartridges or the control units may be provided with a heating member inclusive thereto. In further implementations, a kit may comprise one or more components of separable atomization assemblies. For example, a kit may comprise one or more components containing a mesh plate and one or more components containing a vibrating component. In further implementations, a kit may comprise one or more mouthpiece portions, one or more atomization assemblies, and one or more tank portions. The inventive kits may further include a case (or other packaging, carrying, or storage component) that accommodates one or more of the further kit components. The case could be a reusable hard or soft container. Further, the case could be simply a box or other packaging structure.

Many modifications and other implementations of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol delivery device comprising:

a housing defining an outer wall, and further including a power source and a control component;

a mouthpiece portion that defines an exit aerosol path, the mouthpiece portion being located opposite the housing, such that the mouthpiece portion is located on one end of the device and the housing is located on the other end of the device;

a tank portion that includes a reservoir configured to contain a liquid composition, the tank portion located in the mouthpiece portion and/or the housing; and an atomization assembly located between the mouthpiece portion and the tank portion and configured to vaporize the liquid composition from the tank portion to generate an aerosol, wherein the atomization assembly comprises a mesh plate and a vibrating component, and wherein the mesh plate and the vibrating component are configured to be separable from each other at a detachable interface.

2. The aerosol delivery device of claim 1, wherein at least one of the vibrating component and the mesh plate is further configured to be removable from the device.

3. The aerosol delivery device of claim 1, wherein the vibrating component and the mesh plate are biased into contact with each other using one or more components of the device.

4. The aerosol delivery device of claim 1, wherein the vibrating component and the mesh plate are configured to be compressed between a pair of resilient members.

5. The aerosol delivery device of claim 1, wherein the detachable interface is located between the mouthpiece portion and the tank portion.

6. The aerosol delivery device of claim 5, wherein one of the vibrating component or the mesh plate is located in the mouthpiece portion and the other of the vibrating component or the mesh plate is located in the tank portion.

7. The aerosol delivery device of claim 1, wherein the detachable interface is located within the mouthpiece portion.

8. The aerosol delivery device of claim 1, wherein the detachable interface is located within the tank portion.

9. The aerosol delivery device of claim 1, wherein the mouthpiece portion and the tank portion comprise a cartridge, wherein a remaining portion of the housing comprises a control unit, and wherein the detachable interface is located within the cartridge.

10. The aerosol delivery device of claim 1, wherein the mouthpiece portion and the tank portion comprise a cartridge, wherein a remaining portion of the housing comprises a control unit, and wherein the detachable interface is located within the control unit.

11. The aerosol delivery device of claim 1, wherein the mouthpiece portion and the tank portion comprise a cartridge, wherein a remaining portion of the housing comprises a control unit, and wherein the detachable interface is located between the cartridge and the control unit.

12. The aerosol delivery device of claim 11, wherein one of the vibrating component or the mesh plate is located in the cartridge and the other of the vibrating component or the mesh plate is located in the control unit.

13. The aerosol delivery device of claim 1, wherein the atomization assembly is located between the mouthpiece portion and the tank portion.

14. The aerosol delivery device of claim 13, wherein the mouthpiece portion, the tank portion, and the atomization assembly are separable from each other.

15. The aerosol delivery device of claim 14, wherein the detachable interface is located in the atomization assembly.

16. The aerosol delivery device of claim 1, wherein the vibrating component comprises a piezoelectric material.

17. The aerosol delivery device of claim 16, wherein the vibrating component comprises a piezoceramic ring.

18. The aerosol delivery device of claim 1, wherein the mesh plate is substantially flat.

19. The aerosol delivery device of claim 1, wherein at least a portion of the mesh plate is curved.

20. The aerosol delivery device of claim 19, wherein the curved portion of the mesh plate is convex with respect to the reservoir.

21. The aerosol delivery device of claim 1, wherein the detachable interface comprises at least one of a snap-fit engagement, a press-fit engagement, a threaded engagement, a magnetic engagement, and combinations thereof.

22. The aerosol delivery device of claim 1, wherein the device comprises an open system configured to permit refilling of reservoir with additional liquid composition.

23. The aerosol delivery device of claim 1, wherein the mouthpiece portion and the tank portion comprise a cartridge, wherein a remaining portion of the housing comprises a control unit, and wherein the device comprises a closed system wherein the control unit is configured to accept one or more additional cartridges.

24. The aerosol delivery device of claim 1, wherein the mesh plate comprises a perforated plate.

* * * * *